United States Patent
Zelle

[11] Patent Number: 5,726,184
[45] Date of Patent: Mar. 10, 1998

[54] TETRALIN COMPOUNDS WITH IMPROVED MDR ACTIVITY

[75] Inventor: Robert Edward Zelle, Stowe, Mass.

[73] Assignee: Vertex Pharmaceuticals Incorporated, Cambridge, Mass.

[21] Appl. No.: 444,567

[22] Filed: May 19, 1995

[51] Int. Cl.$^6$ ............ C07D 217/00; C07D 211/00; A61K 31/47; A61K 31/445

[52] U.S. Cl. ............ 514/314; 514/237.2; 514/315; 514/318; 514/330; 544/129; 546/153; 546/192; 546/193; 546/194; 546/146

[58] Field of Search ............ 544/129; 546/153, 546/192, 193, 194, 245, 146; 514/237.2, 314, 315, 318, 330

[56] References Cited

U.S. PATENT DOCUMENTS 5,192,773  3/1993  Armistead et al. .......... 514/315

FOREIGN PATENT DOCUMENTS 9200278  1/1992  WIPO .......... 514/315

Primary Examiner—Zinna Northington Davis
Attorney, Agent, or Firm—Fish & Neave; James F. Haley, Jr.; Andrew S. Marks

[57] ABSTRACT

The present invention relates to compounds that can maintain, increase, or restore sensitivity of cells to therapeutic or prophylactic agents. This invention also relates to pharmaceutical compositions comprising these compounds. The compounds and pharmaceutical compositions of this invention are particularly well-suited for treatment of multi-drug resistant cells, for prevention of the development of multi-drug resistance, and for use in multi-drug resistant cancer.

20 Claims, No Drawings

TETRALIN COMPOUNDS WITH IMPROVED MDR ACTIVITY

TECHNICAL FIELD OF THE INVENTION

The present invention relates to novel compounds which can maintain, increase, or restore sensitivity of cells to therapeutic or prophylactic agents. This invention also relates to pharmaceutical compositions and methods utilizing these compounds. The methods of this invention are directed to the treatment of multi-drug resistant cells, preventing the development of multi-drug resistance and use in multi-drug resistant cancer therapy.

BACKGROUND OF THE INVENTION

A major problem affecting the efficacy of chemotherapy regimens is the evolution of cells which, upon exposure to a chemotherapeutic drug, become resistant to a multitude of structurally unrelated drugs and therapeutic agents. The appearance of such multi-drug resistance often occurs in the presence of over-expression of a 170-kDA membrane P-glycoprotein (gp-170). The gp-170 protein is present in the plasma membranes of some healthy tissues, in addition to cancer cell lines, and is homologous to bacterial transport proteins (Hait et al., *Cancer Communications*, 1(1), p. 35 (1989); West, *TIBS*, 15, p. 42 (1990)). The protein acts as an export pump, conferring drug resistance through active extrusion of toxic chemicals. Although the mechanism for the pump is unknown, it is speculated that the gp-170 protein functions by expelling substances that share certain chemical or physical characteristics, such as hydrophobicity, the presence of carbonyl groups, or the existence of a glutathione conjugate (see West).

Recently, another protein responsible for multi-drug resistance, MRP (multi-drug resistance associated protein), was identified in H69AR cells, an MDR cell line that lacks detectable P-glycoprotein [S. P. C. Cole et al., *Science*, 258, pp. 1650–54 (1992)]. MRP has also been detected in other non-P-glycoprotein MDR cell lines, such as HL60/ADR and MCF-7 breast carcinoma cells [(E. Schneider et al., Cancer Res., 54, pp. 152–58 (1994); and N. Krishnamachary et al., *Cancer Res.*, 53, pp. 3658–61 (1993)].

The MRP gene encodes a 190 kD membrane-associated protein that is another member of the ATP binding cassette superfamily. MRP appears to function in the same manner as P-glycoprotein, acting as a pump for removing natural product drugs from the cell. A possible physiological function for MRP maybe ATP-dependent transport of glutathione S-conjugates [G. Jedlitschky et al., *Cancer Res.*, 54, pp. 4833–36 (1994); I. Leier et al., *J. Biol. Chem.*, 269, pp. 27807–10 (1994); and Muller et al., *Proc. Natl. Acad. Sci. USA*, 91, pp. 13033–37 (1994)].

The role of MRP in clinical drug resistance remains to be clearly defined, but it appears likely that MRP may be another protein responsible for a broad resistance to anti-cancer drugs.

Various chemical agents have been administered to repress multi-drug resistance and restore drug sensitivity. While some drugs have improved the responsiveness of multi-drug resistant ("MDR") cells to chemotherapeutic agents, they have often been accompanied by undesirable clinical side effects (see Hait et al.). For example, although cyclosporin A ("CsA"), a widely accepted immunosuppressant, can sensitize certain carcinoma cells to chemotherapeutic agents (Slater et al., *Br. J. Cancer*, 54, p. 235 (1986)), the concentrations needed to achieve that effect produce significant immunosuppression in patients whose immune systems are already compromised by chemotherapy (see Hait et al.). In addition, CsA usage is often accompanied by adverse side effects including nephrotoxicity, hepatotoxicity and central nervous system disorders. Similarly, calcium transport blockers and calmodulin inhibitors both sensitize MDR cells, but each produces undesirable physiological effects (see Hait et al.; Twentyman et al., *Br. J. Cancer*, 56, p. 55 (1987)).

Recent developments have led to agents said to be of potentially greater clinical value in the sensitization of MDR cells. These agents include analogs of CsA which do not exert an immunosuppressive effect, such as 11-methyl-leucine cyclosporin (11-met-leu CsA) (see Hait et al.; Twentyman et al.), or agents that may be effective at low doses, such as the immunosuppressant FK-506 (Epand and Epand, *Anti-Cancer Drug Design*, 6, p. 189 (1991)). PCT publication WO 94/07858 refers to a novel class of MDR modifying agents with some structural similarities to the immunosuppressants FK-506 and rapamycin. Despite these developments, there is still a need for more effective agents which may be used to re-sensitize MDR cells to therapeutic or prophylactic agents or to prevent the development of multi-drug resistance.

SUMMARY OF THE INVENTION

The present invention solves the problem referred to above by providing compounds that are more potent than previously described MDR modifiers in preventing and reversing multi-drug resistant ("MDR"). The compounds of this invention may be formulated into pharmaceutical compositions useful to maintain the therapeutic or prophylactic effects of drugs in cells, or to restore those effects in MDR cells. Such compositions may optionally contain additional therapeutic or prophylactic agents.

According to another embodiment, the invention provides methods of utilizing the above pharmaceutical compositions for treating or preventing both P-glycoprotein- and MRP-mediated MDR. Such methods are especially useful to enhance the efficacy of chemotherapy regimens employed in the treatment of cancer or other diseases.

The present invention also provides methods for preparing the compounds of this invention.

DETAILED DESCRIPTION OF THE INVENTION

This invention provides a novel class of compounds represented by formula (I):

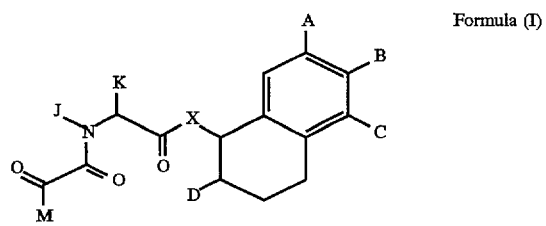

Formula (I)

and pharmaceutically acceptable salts thereof, wherein:

A, B and C are independently selected from hydrogen, halogen, (C1–C6)-straight or branched alkyl, O—(C1–C6)-straight or branched alkyl, $(CH_2)_n$—Ar or $Y(CH_2)_n$—Ar; wherein Y is O, S or $NR_1$; wherein $R_1$ is (C1–C6)-straight or branched alkyl and hydrogen;

n is an integer from 0 to 4; and

Ar is a carbocyclic aromatic group selected from the group consisting of phenyl, 1-naphthyl, 2-naphthyl, indenyl, azulenyl, fluorenyl and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, peridinyl, carbazolyl, acridinyl, phenazinyl, phenothiazinyl and phenoxazinyl; and
wherein:
  Ar may contain one or more substituents independently selected from the group consisting of: hydrogen, hydroxyl, halogen, nitro, $SO_3H$, trifluoromethyl, trifluoromethoxy, (C1–C6)-straight or branched alkyl, O—(C1–C6)-straight or branched alkyl, O-benzyl, O-phenyl, 1,2-methylenedioxy, carboxyl, morpholinyl, piperidinyl and $NR_2R_3$ and $NR_2R_3$ carboxamides; wherein
    $R_2$ and $R_3$ are independently selected from hydrogen, (C1–C5)-straight or branched alkyl and benzyl;
D is selected from the group consisting of hydrogen or $(CH_2)_m$—E; wherein
  E is Ar or $NR_4R_5$; wherein
    $R_4$ and $R_5$ are independently selected from hydrogen, (C1–C5)-straight or branched alkyl and $(CH_2)$Ar or can be taken together to form a 5 or 6 membered heterocyclic ring; and
  m is an integer from 1 to 3;
X is O or $NR_6$; wherein
  $R_6$ is selected from the group consisting of hydrogen, (C1–C6)-straight or branched alkyl and $(CH_2)_m$—Ar;
J and K are independently (C1–C6)-straight or branched alkyl or Ar-substituted with (C1–C6)-straight or branched alkyl or wherein J and K are taken together to form a five or six membered ring or a five or six membered benzo-fused ring;
M is (C1–C6)-straight or branched alkyl or Ar; and
the stereochemistry at carbon 1 and carbon 2 is independently selected from R or S.

More preferred compounds of this invention are represented by formula (II):

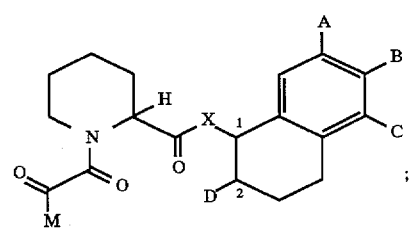

Formula (II)

formula (III):

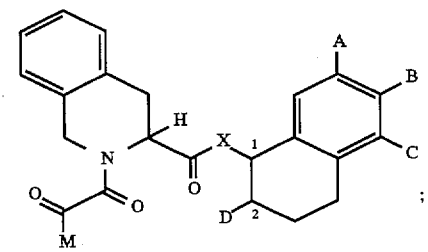

Formula (III)

and formula (IV):

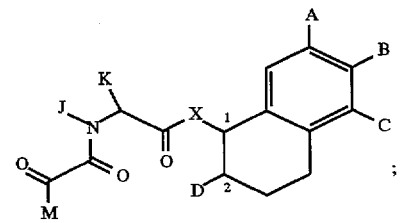

Formula (IV)

wherein, in formula (IV), J is methyl or hydrogen and K is $(CH_2)_m$—Ar or (C1–C6)-straight or branched alkyl. More preferably, K is substituted or unsubstituted benzyl. Most preferably, K is benzyl or 4-halo-benzyl.

Preferably choices for other indicated substituents of formula I-IV are as follows:

A is preferably $OCH_2$-4-pyridine, O-propyl or hydrogen;

B is preferably $OCH_2$-4-pyridine, methyl or hydrogen;

C is preferably $OCH_2$-4-pyridine, O-propyl or hydrogen;

D is preferably $CH_2$-3-pyridine or hydrogen;

X is preferably oxygen, $NH_2$ or N-benzyl; and

M is preferably 3,4,5-trimethoxyphenyl.

The most preferred compounds of this invention are indicated in Table 1, below.

TABLE 1

| Cpd | Formula | A | B | C | D | J | K | X |
|---|---|---|---|---|---|---|---|---|
| 6 | II | $OCH_2$-4-Pyr | H | H | H | | | O |
| 7 | II | $OCH_2$-4-Pyr | H | H | H | | | O |
| 9 | II | H | H | $OCH_2$-4-Pyr | H | | | O |
| 11A | II | $OCH_2$-4-Pyr | H | H | H | | | NH |
| 11B | II | $OCH_2$-4-Pyr | H | H | H | | | NH |
| 15 | II | $OCH_2$-4-Pyr | H | H | H | | | N-benzyl |
| 16 | II | $OCH_2$-4-Pyr | H | H | H | | | N-benzyl |
| 17 | III | $OCH_2$-4-Pyr | H | H | H | | | O |
| 18 | III | $OCH_2$-4-Pyr | H | H | H | | | O |

TABLE 1-continued

| Cpd | Formula | A | B | C | D | J | K | X |
|---|---|---|---|---|---|---|---|---|
| 19 | IV | OCH$_2$-4-Pyr | H | H | H | H | benzyl | O |
| 20 | IV | OCH$_2$-4-Pyr | H | H | H | CH$_3$ | benzyl | O |
| 21 | IV | OCH$_2$-4-Pyr | H | H | H | CH$_3$ | benzyl | O |
| 29A | II | O-propyl | methyl | O-propyl | (CH$_2$)-3-Pyr | | | O |
| 29B | II | O-propyl | methyl | O-propyl | (CH$_2$)-3-Pyr | | | O |
| 30A | II | O-propyl | methyl | O-propyl | (CH$_2$)-3-Pyr | | | O |
| 30B | II | O-propyl | methyl | O-propyl | (CH$_2$)-3-Pyr | | | O |

As defined herein, the compounds of this invention include all optical and racemic isomers.

In addition to the compounds described herein, the invention also includes pharmaceutically acceptable derivatives of those compounds. A "pharmaceutically acceptable derivative" denotes any pharmaceutically acceptable salt, ester, or salt of such ester, of a compound of this invention or any other compound which, upon administration to a patient, is capable of providing (directly or indirectly) a compound of this invention, or a metabolite or residue thereof, characterized by the ability to maintain, increase or restore sensitivity of MDR cells to therapeutic or prophylactic agents or to prevent development of multi-drug resistance.

Compounds of this invention represented by formula (I) may be obtained using any conventional technique. Preferably, these compounds are chemically synthesized from readily available starting materials, such as alpha-amino acids. Modular and convergent methods for the synthesis of these compounds are also preferred. In a convergent approach, for example, large sections of the final product are brought together in the last stages of the synthesis, rather than by incremental addition of small pieces to a growing molecular chain.

Scheme 1 illustrates a representative example of a convergent process for the synthesis of compounds of formula (I). The process comprises coupling of a protected amino acid of formula (VI), wherein P is a protecting group, with an amine or alcohol of formula (V), wherein X is O or NR$_6$ to provide an ester (when X=O) or an amide (when X=NR$_6$) of formula (VII), Protected alpha-amino acids are well known in the art and many are commercially available. For example, common protecting groups and convenient methods for the protection of amino acids are described in T. W. Greene, P. G. M. Wuts, "Protective Groups in Organic Chemistry, 2nd Ed.", John Wiley and Sons, New York (1991). Alkoxycarbonyl groups are preferred for protection of the nitrogen atom in compounds of formula (VII), with t-butoxycarbonyl (Boc), benzyloxycarbonyl (Cbz), allyloxycarbonyl (Alloc), and trimethylsilylethoxy-carbonyl (Teoc) being more preferred.

After the coupling, compounds of formula (VII) are deprotected under suitable deprotection conditions (see Greene, supra), and the free amino group of (VIII) is then acylated using an activated form of formula (IX) to provide compounds of formula (I).

Alcohols and amines of formula (V) can conveniently be prepared as illustrated in Schemes 2, 3 and 4. Alkylation of hydroxy-tetralone (XI), containing substituents, A, B and C (where A in this example is hydroxy) with appropriate alkylating agents provides ethers of formula (XII), Scheme 2. Reduction of the carbonyl with DIBAL-H or other reducing agents used in the art provides the desired alcohol of formula (XIII), Amines of formula (XV) have been prepared by reductive amination of ketone (XIV) as illustrated in Scheme 3. Preparation of alcohols of formula (V) wherein D is not hydrogen are illustrated in Scheme 4. Treatment of ketone (XVI) with a Schiff base under acidic conditions such as trifluoroacetic acid or Ar-aldehydes under basic conditions provides enones of formula (XVII). Catalytic hydrogenation provides the ketone (XVIII) which upon reduction with various hydride reducing agents provides a mixture of syn (XIXb) and anti (XIXa) alcohols.

Scheme 1

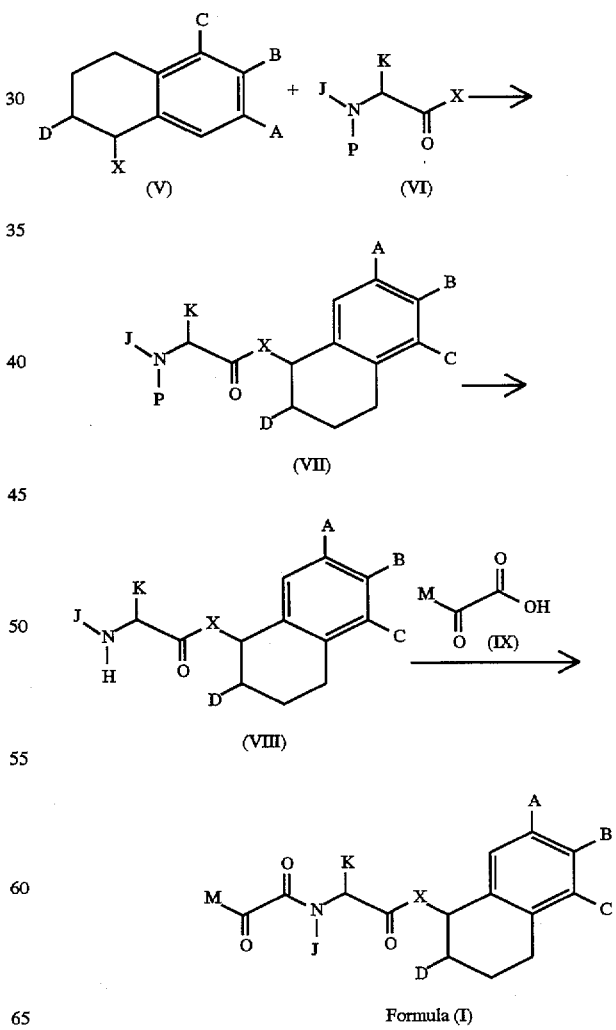

Formula (I)

Scheme 2

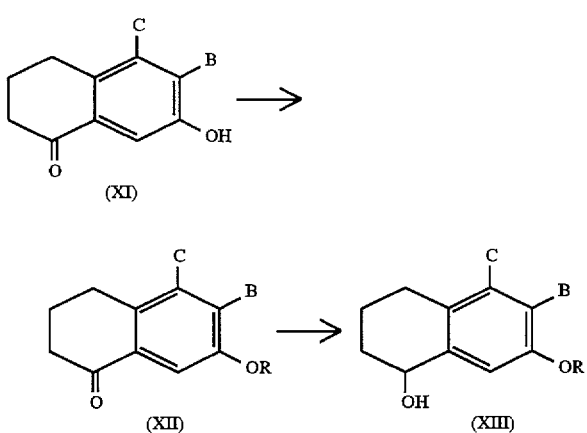

Scheme 3

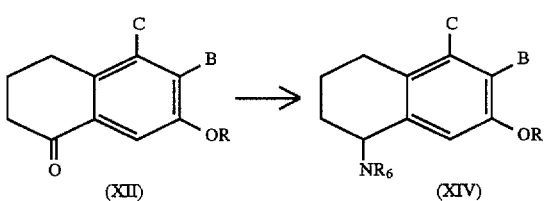

Scheme 4

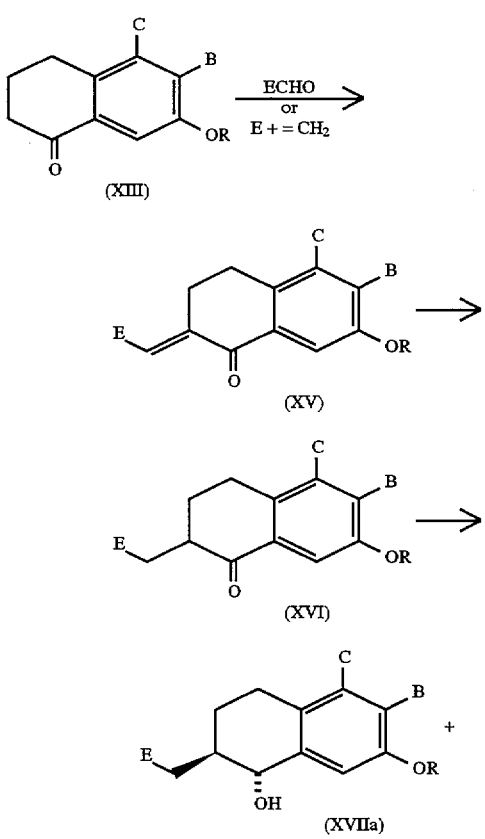

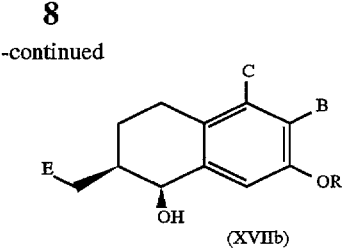

Thus, this invention also provides a method for preparing compounds of formula (I) comprising the steps of:

(a) coupling an amino acid of formula (VI) with an alcohol or amine of formula (V), wherein X is O or $NR_6$ to give the corresponding ester or amide of formula (VII);

(b) deprotecting the amide of formula (VII) to give an amine of formula (VIII); and (c) acylating the amine of formula (VIII) with a compound of formula (IX).

It should be appreciated by those of ordinary skill in the art that a large variety of compounds of formula (I) may be readily prepared, according to the processes illustrated in synthetic Schemes 1–4. The same processes may be used for the synthesis of many different end-products, by altering the variables in the starting materials.

Optically active compounds of formula (I) may also be prepared using optically active starting materials, thus obviating the need for resolution of enantiomers or separation of diastereomers at a late stage in the synthesis.

Scheme 5 illustrates one example of the preparation of enantiomerically pure alcohols of formula (II'a). Treatment of alcohol (II'a) with various lipases has provided a mixture of (S)-alcohol (II'b) and (R)-acetate (II'c). Separation and hydrolysis of (II'c) provides the corresponding (R)-alcohol.

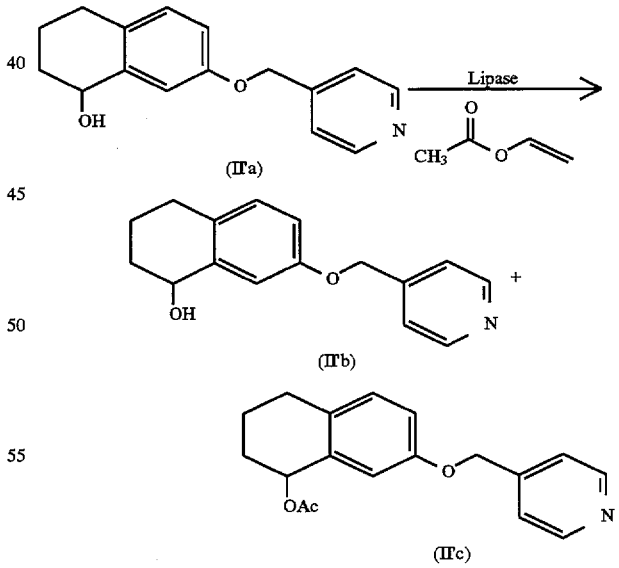

It will also be appreciated by those of ordinary skill in the art that the above synthetic schemes are not intended to comprise a comprehensive list of all means by which the compounds or the intermediates of this invention may be synthesized. Further methods or modifications of the above general schemes will be evident to those of ordinary skill in the art.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of this invention are characterized by the ability to increase, restore or maintain the sensitivity of MDR cells to cytotoxic compounds, such as, for example, those typically used in chemotherapy. Based on that ability, the compounds of this invention are advantageously used as chemosensitizing agents, to increase the effectiveness of chemotherapy in individuals who are afflicted with drug-resistant cancers, tumors, metastases or disease. In addition, the compounds of this invention are capable of maintaining sensitivity to therapeutic or prophylactic agents in non-resistant cells. Therefore, the compounds of this invention are useful in treating or preventing multi-drug resistance ("MDR") in a patient. More specifically, these compounds are useful in treating of preventing P-glycoprotein-mediated MDR and MRP-mediated MDR.

As used throughout this application, the term "patient" refers to mammals, including humans. And the term "cell" refers to mammalian cells, including human cells.

As used herein, the terms "sensitizing agent", "sensitizer", "chemosensitizing agent", "chemosensitizer" and "MDR modifier" denote a compound having the ability to increase or restore the sensitivity of an MDR cell, or to maintain the sensitivity of a non-resistant cell, to one or more therapeutic or prophylactic agents. The term "MDR sensitization" and "sensitization" and "resensitization" refer to the action of such a compound in maintaining, increasing, or restoring drug sensitivity.

The compounds of the present invention may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term "parenteral" as used herein includes subcutaneous, intravenous, intramuscular, intra-articular, intra-synovial, intrasternal, intrathecal, intrahepatic, intralesional and intracranial injection or infusion techniques.

The pharmaceutical compositions of this invention comprise any of the compounds of the present invention, or pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention included but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, 5% dextrose solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex and diet of the patient, the time of administration and rate of excretion of the compound, the particular drug combination, and the judgment of the treating physician and the severity of the particular disease being treated. The amount of active ingredient may also depend upon the therapeutic or prophylactic agent, if any, with which the ingredient is co-administered. The term "pharmaceutically effective amount" refers to an amount effective to prevent multi-drug resistance or to maintain, increase or restore drug sensitivity in MDR cells.

When the compounds of this invention are administered in combination therapies with other agents, they may be administered sequentially or concurrently to the patient. Alternatively, pharmaceutical or prophylactic compositions according to this invention may comprise a combination of a compound of this invention and another therapeutic or prophylactic agent.

For example, the compounds may be administered either alone or in combination with one or more therapeutic agents, such as chemotherapeutic agents, (e.g., actinomycin D, doxorubicin, vincristine, vinblastine, etoposide, amsacrine, mitoxantrone, tenipaside, taxol and colchicine) and/or a chemosensitizing agent (e.g., cyclosporin A and analogs, phenothiazines and thioxantheres), in order to increase the susceptibility of the MDR cells within the patient to the agent or agents.

According to another embodiment, the invention provides methods for treating or preventing multi-drug resistance in a patient by administering a composition comprising an effective amount of a compound of this invention. Effective dosage levels for treating or preventing MDR range from between about 0.01 and about 100 mg/kg body weight per days preferably between about 0.5 and about 50 mg/kg body weight per day of a compound of this invention. A typical composition for use in treating MDR will contain between about 5% and about 95% of active compound(s) (w/w), whether it be solely one of the compounds of this invention or a combination of a compound of this invention and another chemotherapeutic or chemosensitizing agent. Preferably, such preparations contain between about 20% and about 80% active compound(s).

In order that this invention may be more fully understood, the following examples are set forth. These examples are for the purpose of illustration only and are not to be construed as limiting the scope of the invention in any way.

EXAMPLES

General Methods

Proton nuclear magnetic resonance ($^1$H NMR) spectra were recorded at 500 MHZ on a Bruker AMX 500. Chemical shifts are reported in parts per million (δ) relative to Me$_4$Si (δ0.0). Analytical high performance liquid chromatography was performed on either a Waters 600E or a Hewlett Packard 1050 liquid chromatograph.

Example 1

7-(Pyridin-4-ylmethoxy)-1,2,3,4-tetrahydronaphthalen-1-one (Compound 1)

To a solution of 7-hydroxy-1-tetralone (15.0 g, 92.59 mmol) in dimethylsulfoxide (150 mL) was added in portions powdered potassium carbonate (30.66 g, 0.11 mol) followed by the addition of 4-picoyl chloride hydrochloride (18.22 g, 0.22 mol). The resulting mixture was heated at 50° C. for 30 min. The resulting dark brown mixture was diluted with water (200 mL) and extracted with ethyl acetate (500 mL). The aqueous phase was re-extracted with ethyl acetate (300 mL) and the extracts combined, dried over anhydrous magnesium sulfate, filtered and concentrated in vacuo. Chromatography of the residue on silica gel (elution with 40–60% ethyl acetate: hexanes) provided 20.82 g of Compound 1 as an oil which crystallized upon standing.

Example 2

7-(Pyridin-4-ylmethoxy)-1,2,3,4-tetrahydronaphthalen-1-ol (Compound 2)

To a solution of Compound 1 (16.41 g, 64.9 mmol) in tetrahydrofuran (75 mL) at 0° C. was added dropwise a 1M solution of diisobutylaluminum hydride in toluene (97.3 mL). After 1 hr, the reaction was quenched with aqueous potassium sodium tartrate and diluted with ethyl acetate followed by warming to room temperature. After stirring for an additional hour, the layers were separated and the aqueous phase was re-extracted with ethyl acetate (2×). The extracts were combined, washed with brine, dried over anhydrous magnesium sulfate, filtered and concentrated in vacuo. Chromatography of the residue on silica gel (elution with ethyl acetate) provided 12.96 g of Compound 2 as an oil which crystallized upon standing.

Example 3

7-(Pyridin-4-ylmethoxy)-1,2,3,4-tetrahydronaphthalen-1(S)-ol (Compound 2 (S)) and 1(R)-Accedas-7-(Pyridin-4-ylmethoxy)-1,2,3,4-tetrahydronaphthalene (Compound 3(R))

A solution of Compound 2 (12.96, 50.82 mmol) in tetrahydrofuran (20 mL) was diluted with tert-butylmethyl ether (260 mL) followed by the addition of vinyl acetate (19.1 mL, 0.21 mol) and Amano PS-30 Lipase (13.0 g). After stirring for 8 hrs, the reaction was filtered and concentrated in vacuo to provide an oil. Chromatography on silica gel (elution with 20% acetone:hexanes) provided 7.41 g of acetate 3(R) as a white crystalline material. Further elution with 60% acetone:hexanes provided 6.1 g of Compound 2(S) as a white crystalline material. The enantiomeric purity of compound 2(S) was established by HPLC using a Chiralpak OD column to be >99.8% ee.

Example 4

7-(Pyridin-4-ylmethoxy)-1,2,3,4-tetrahydronaphthalen-1(R)-ol (Compound 2 (R))

To a solution of Compound 3(R) (6.1 g, 20.9 mmol) in methanol (35 mL) was added powdered potassium carbonate (2.88 g, 20.9 mmol). After stirring for 45 min, the reaction was concentrated in vacuo. The residue was taken-up into methylene chloride and 50% brine. The layers were separated and the aqueous phase re-extracted with methylene chloride. The organics were combined, washed with brine, dried over anhydrous magnesium sulfate, filtered and concentrated in vacuo to provide 4.7 g of Compound 2(R) as a white crystalline material. The enantiomeric purity of compound 2(S) was established by HPLC using a Chiralpak OD column to be >99.4% ee.

Example 5

(S)-Piperidine-1,2-dicarboxylic acid 1-allyl ester 2-((7-pyridin-4-ylmethoxy)-1,2,3,4-tetrahydronaphthalen-1-yl) ester (Compound 4)

To a solution of Compound 2 (663 mg, 2.6 mmol), Alloc-(S)-pipecolic acid (610 mg, 2.86 mmol) and dimethylaminopyridine (32 mg, 0.26 mmol), in methylene chloride (5 mL) was added (3-dimethylaminopropyl)-3-ethyl-carbodiimide hydrochloride (548 mg, 2.86 mmol). After stirring for 24 hr, the reaction was diluted with ethyl acetate and water. The layers were separated and the aqueous phase was re-extracted with ethyl acetate. The extracts were combined, washed with sat. sodium bicarbonate, water, brine, dried over anhydrous magnesium sulfate, filtered and concentrated in vacuo. Chromatography of the residue on silica gel (elution with 20% acetone:hexanes) provided 940 mg of Compound 4 as a mixture of diastereomers.

Example 6

(S)-Piperidine-2-carboxylic acid 2-((7-pyridin-4-ylmethoxy)-1,2,3,4-tetrahydronaphthalen-1-yl) ester (Compound 5)

To a solution of Compound 4 (940 mg, 2.09 mmol) in tetrahydrofuran (5.0 mL)was added morpholine (1.1 mL, 12.6 mmol) and tetrakistriphenylphosphine pallidium (0) (241 mg, 0.21 mmol). After 1 hr, the heterogenous mixture was diluted with ethyl acetate, washed with 50% brine, 5% sodium bicarbonate, brine, dried over anhydrous magnesium sulfate, filtered and concentrated in vacuo. Chromatography of the residue on silica gel (elution with 50–100% acetone:hexanes) provided 510 mg of Compound 5.

Example 7

1-(2-Oxo-2-(3,4,5-trimethoxyphenyl )-acetyl)-piperidine-2 (S)-carboxylic acid 2-((7-pyridin-4-ylmethoxy)-1,2,3,4-tetrahydronaphthalen-1(S)-yl) ester (Compound 6) and 1-(2-Oxo-2-(3,4,5-trimethoxyphenyl)-acetyl)-piperidine-2(S)-carboxylic acid 2-((7-pyridin-4-yl methoxy)-1,2,3,4-tetrahydronaphthalen-1(R)-yl) ester (Compound 7)

To a solution of Compound 5 (510 mg, 1.4 mmol) and 3,4,5-trimethoxybenzyolformic acid (505 mg, 2.1 mmol) in methylene chloride (6 mL) was added (3-dimethylaminopropyl)-3-ethyl-carbodiimide hydrochloride (400 mg, 2.1 mmol). After stirring for 24 hr, the reaction was diluted with ethyl acetate and water. The layers were separated and the aqueous phase was re-extracted with ethyl acetate. The extracts were combined, washed with sat. sodium bicarbonate, water, brine, dried over anhydrous magnesium sulfate, filtered and concentrated in vacuo. Chromatography of the residue on silica gel (elution with 25% acetone:hexanes) provided 558 mg of product as a mixture of diastereomers. Reverse phase MPLC provided diastereomerically pure Compound 6 and Compound 7.

Alternatively, replacement of Compound 2 with resolved Compound 2(S) in Examples 5–6 and the above example provided Compound 6 directly, whereas Compound 2(R) provided Compound 7.

Compound 6: $^1$H NMR as a mixture of rotomers (500 MHz, CDCl$_3$) δ8.53 (d), 8.55(d), 7.38 (s), 7.34–7.28 (m), 7.17 (s), 7.05 (d), 7.01 (d), 6.88–6.79 (m), 6.64 (d) 6.00 (t), 5.93 (t), 5.39 (br d), 5.05–5.00 (m), 4.58 (br d), 4.34 (br d), 3.93–3.88 (m), 3.79 (s), 3.49 (br d), 3.28 (dt), 3.02 (dt), 2.80 (dt), 2.73–2.60 (m), 2.36–2.28 (m), 2.08–1.49 (m), 1.37–1.27 (m).

Compound 7: $^1$H NMR as a mixture of rotomers (500 MHz, CDCl$_3$) δ8.56–8.54 (m), 7.35 (s), 7.29–7.28 (m), 7.16 (s), 7.05 (d), 7.00 (d), 6.86–6.81 (m), 6.73 (d), 6.00 (t), 5.87 (t), 5.35 (br d), 5.07–4.93 (m), 4.58 (br d), 4.34 (m), 3.94–3.89 (m), 3.84 (s), 3.45 (br d), 3.22 (dt), 3.09 (dt), 2.79 (dt), 2.72–2.60 (m), 2.25 (m), 2.10 (m), 2.03–1.47 (m), 1.40–1.30 (m), 1.27–1.17 (m).

Example 8

1-(2-Oxo-2-(3,4,5-trimethoxyphenyl)-acetyl)-piperidine-2 (S)-carboxylic acid 2-((6-pyridin-4-ylmethoxy)-1,2,3,4-tetrahydronaphthalen-1-yl) ester (Compound 8)

Compound 8 was prepared as described in Examples 1–2 and 5–7 utilizing 6-hydroxy-1-tetralone in place of 7-hydroxy-1-tetralone to provide Compound 8 as a mixture of diastereomers. $^1$H NMR as a mixture of diastereomers and rotomers (500 MHz, CDCl$_3$) δ8.59 (d), 7.38 (s), 7.37 (s), 7.33 (m), 7.22 (d), 7.18 (dd), 7.04 (d), 6.77 (dt), 6.70 (m), 6.64 (m), 6.04 (m), 5.92 (t), 5.88 (t), 5.35 (m), 5.06 (s), 5.05 (s), 5.03 (s), 4.58 (m), 4.31 (dd), 3.94 (s), 3.93 (s), 3.92 (s), 3.87 (s), 3.86 (s), 3.47 (br d), 3.27 (dq), 3.13 (dt), 3.07 (dt), 2.87–2.61 (m), 2.34 (br d), 2.26 (br d), 2.18–1.18 (m).

Example 9

1-(2-Oxo-2-(3,4,5-trimethoxyphenyl)-acetyl)-piperidine-2 (S)-carboxylic acid 2-((5-pyridin-4-ylmethoxy)-1,2,3,4-tetrahydronaphthalen-1-yl) ester (Compound 9)

Compound 9 was prepared as described in Examples 1–2 and 5–7 utilizing 5-hydroxy-1-tetralone in place of 7-hydroxy-1-tetralone to provide Compound 9 as a mixture of diastereomers. $^1$H NMR as a mixture of diastereomers and rotamers (500 MHz, CDCl$_3$) δ8.64 (m), 7.39 (m), 7.27 (s), 7.20 (d), 7.17 (q), 6.98 (d), 6.92 (d), 6.80 (t), 6.73 (dd), 6.40 (d), 6.10 (q), 5.99 (t), 5.95 (t), 5.40 (m), 5.12 (m), 5.12 (s), 5.08 (d), 4.60 (m), 4.35 (m), 3.96 (s), 3.85 (s), 3.94 (s), 3.90 (s), 3.89 (s), 3.50 (br d), 3.30 (dq), 3.19–3.08 (m), 3.0–2.86 (m), 2.74–2.58 (m), 2.38 (m), 2.30 (m), 2.10–1.50 (m), 1.45–1.25 (m).

Example 10

1-Amino-7-(pyridin-4-ylmethoxy)-1,2,3,4-tetrahydronaphthalene (Compound 10)

To a solution of Compound 1 (1.71 g, 6.75 mmol) and methoxyamine hydrochloride (845 mg, 10.12 mmol) in abs. ethanol (20 mL) was added powdered potassium carbonate (2.25 g, 16.88 mmol) and the reaction heated to reflux. After 2 hr, the reaction was cooled and concentrated in vacuo. The residue was diluted with ethyl acetate, washed with 5% sodium bicarbonate, water, brine, dried over anhydrous magnesium sulfate, filtered and concentrated in vacuo. Chromatography of the residue on silica gel (elution with 40% ethyl acetate:hexanes) provided 1.9 g of oxime.

To a solution of the above oxime in tetrahydrofuran (5 mL) was added a 1M solution of borane in tetrahydrofuran (20.25 mL) and the reaction heated to reflux and stirred for 18 hr. The reaction was cooled and quenched with saturated methanolic hydrochloric acid (20 mL) and the reaction reheated to reflux and stirred an additional 30 min. The reaction was cooled and concentrated to dryness. The residue was taken up into water (10 mL) and washed with diethyl ether (3×20 mL). The aqueous phase was adjusted to pH 8.0 with sat. sodium bicarbonate and extracted with ethyl acetate (3×50 mL). The extracts were combined, washed with brine, dried over anhydrous magnesium sulfate, filtered and concentrated in vacuo to provide 945 mg of Compound 10.

Example 11

1-(2-Oxo-2-(3,4,5-trimethoxyphenyl)-acetyl)-piperidine-2 (S)-carboxylic acid 2-((7-pyridin-4-ylmethoxy)-1,2,3,4-tetrahydronaphthalen-1(R)-yl) amide and 1-(2-Oxo-2-(3,4,5-trimethoxyphenyl)-acetyl)-piperidine-2(S)-carboxylic acid 2-((7-pyridin-4-ylmethoxy)-1,2,3,4-tetrahydronaphthalen-1(S)-yl) amide (Compound 11A and 11B)

Compounds 11A and 11B were prepared as described in Example 5–7 by replacing Compound 2 with Compound 10 to provide a mixture of diastereromers. Chromatography of the residue on silica gel (elution with 20% acetone:hexanes) provided Compound 11A. Further elution provided Compound 11B.

Compound 11A: $^1$H NMR as a mixture of rotomers (500 MHz, CDCl$_3$) δ8.57 (m), 7.36(d), 7.34 (s), 7.30 (d), 7.13 (s), 7.02 (t), 6.97 (d), 6.82 (dd), 6.79 (dd), 6.73 (d), 6.11 (d), 5.21 (m), 5.18–5.08 (m), 5.02 (s), 4.66 (br d), 4.18 (d), 3.92 (s), 3.87 (s), 3.81 (s), 3.60 (br d), 3.32 (dt), 2.81–2.64 (m), 2.40 (br d), 2.26 (m), 2.11–2.01 (m), 1.84–1.65 (m), 1.51–1.42 (m).

Compound 11B: $^1$H NMR as a mixture of rotomers (500 MHz, CDCl$_3$) δ8.58 (m), 8.48 (m), 7.34 (s), 7.33 (m), 7.29 (m), 7.21 (d), 7.17 (s), 7.02 (t), 6.86 (d), 6.86–6.76 (m), 6.01 (d), 5.19–5.10 (m), 5.02 (m), 4.99 (q), 4.58 (br d), 4.18 (d), 3.93 (s), 3.89 (s), 3.86 (s), 3.48 (br d), 3.41 (dt), 2.80–2.62 (m), 2.41 (br d), 2.21 (br d), 2.12–2.00 (m), 1.88–1.40 (m).

Example 12

N-Benzyl-1-amino-7-(pyridin-4-ylmethoxy)-1,2,3,4-tetrahydronaphthalene (Compound 12)

A solution of Compound 1 (820 mg, 3.24 mmol) and benzyl amine (354 µL, 3.24 mmol) in benzene (10 mL) was heated to reflux under azeotropic conditions. After the calculated amount of water was collected, the reaction was cooled and concentrated in vacuo. The residue was taken-up into ethanol (5 mL) and added to a slurry of sodium boroydride (246 mg, 6.48 mmol) in ethanol (15 mL). The reaction was heated to 80° C., stirred for 30 min, cooled and concentrated in vacuo. The residue was diluted with ethyl acetate followed by the slow addition of 1N hydrochloric acid. The layers were separated. The aqueous phase was adjusted to pH 7 with 2N sodium hydroxide and extracted with methylene chloride (2×). The organics were combined, washed with brine, dried over anhydrous magnesium sulfate, filtered and concentrated in vacuo. Chromatography on silica gel (elution with 5% methanol:methylene chloride) provided 1.09 g of Compound 12 as an oil.

Example 13

(S)-Piperidine-1,2-dicarboxylic acid 1-tert-butyl ester 2-(N-benzyl-(7-pyridin-4-ylmethoxy)-1,2,3,4-tetrahydronaphthalen-1(R)-yl) amide and (S)-Piperidine-1,2-dicarboxylic acid 1-tert-butyl ester 2-(N-benzyl-(7-pyridin-4-ylmethoxy)-1,2,3,4-tetrahydronaphthalen-1(S)-yl) amide (Compound 13A and 13B)

To a solution of Compound 12 (1.09 g, 3.16 mmol) and Boc-(S)-pipecolic acid (868 mg, 3.79 mmol) in methylene chloride (10 mL) was added (3-dimethylaminopropyl)-3-ethyl-carbodiimide hydrochloride (725 mg, 3.79 mmol). After stirring for 72 hr, the reaction was diluted with ethyl acetate and water. The layers were separated and the aqueous phase was re-extracted with ethyl acetate. The extracts were combined, washed with sat. sodium bicarbonate, water, brine, dried over anhydrous magnesium sulfate, filtered and concentrated in vacuo. Chromatography of the residue on silica gel (elution with 40% acetone:hexanes) provided 601 mg of Compound 13A and further elution provide 181 m g of Compound 13B as white solids.

Example 14

(S)-Piperidine-2-dicarboxylic acid 2-(N-benzyl-(7-pyridin-4-ylmethoxy)-1,2,3,4-tetrahydronaphthalen-1-yl) amide (Compound 14)

To a solution of Compound 13A (601 mg, 1.08 mmol) in methylene chloride (10 mL) was added trifluoroacetic acid (1 mL). After stirring for 1.5 hr, the reaction was concentrated in vacuo. The residue was neutalized with sat. potassium carbonate and extracted with ethyl acetate (2×). The extracts were combined washed with brine, dried over anhydrous magnesium sulfate, filtered and concentrated in vacuo, to provide 450 mg of Compound 14.

Example 15

1-(2-Oxo-2-(3,4,5-trimethoxyphenyl)-acetyl)-piperidine-(S)-carboxylic acid 2-(N-benzyl (7-pyridin-4-ylmethoxy)-1,2,3,4-tetrahydronaphthalen-1-yl) amide (Compound 15)

Compound 15 was prepared according to Example 7, but replacing Compound 5 with 14. $^1$H NMR as a mixture of rotomers (500 MHz, CDCl$_3$)δ8.52 (d), 8.39 (dd), 7.51 (m), 7.44 (s), 7.37 (s), 7.37 (t), 7.30–7.15 (m), 7.09 (d), 7.05 (d), 6.99 (d), 6.89 (dd), 6.74 (m), 6.39 (m), 5.69 (d), 5.41 (m), 5.21 (m), 5.15 (q), 4.90 (q), 4.72 (d), 4.64 (d), 3.95–3.86 (m), 3.70–3.67 (m), 3.57 (br d), 3.54 (d), 3.48 (m), 2.74–2.64 (m), 2.20–1.58 (m).

Example 16

1-(2-Oxo-2-(3,4,5-trimethoxyphenyl)-acetyl)-piperidine-(S)-carboxylic acid (2-N-benzyl (7-pyridin-4-ylmethoxy)-1,2,3,4-tetrahydronaphthalen-1-yl) amide (Compound 16)

Compound 16 was prepared according to Example 14–15, but replacing Compound 13A with 13B. $^1$H NMR as a mixture of rotomers (500 MHz, CDCl$_3$) δ8.63 (d), 7.37–7.33 (m), 7.30–7.22 (m), 7.13–7.10 (m), 7.03 (dd), 6.87 (br s), 6.79 (dt), 5.83 (m), 5.06 (q), 4.96 (q), 4.90 (d), 4.83 (q), 4.38 (d), 4.13 (d), 3.94 (s), 3.90 (s), 3.87 (s), 3.85 (s), 2.70–2.62 (m), 2.14 (m), 1.91 (m), 1.88–1.68 (m), 1.54–1.44 (m), 1.35–1.22 (m).

Example 17

2-(2-Oxo-2-(3,4,5-trimethoxyphenyl)-acetyl)-1,2,3,4-tetrahydroisoquinoline-3(S)-carboxylic acid 2-((7-pyridin-4-ylmethoxy)-1,2,3,4-tetrahydronaphthalen-1(R)-yl) ester (Compound 17)

Compound 17 was prepared according to Examples 5–7, but replacing (S)-Alloc-pipecolic acid with (S)-Alloc-3-carboxyl-1,2,3,4-tetrahydroisoquinoline and utilizing Compound 2(R). $^1$H NMR as a mixture of rotomers (500 MHz, CDCl$_3$) δ8.62 (d), 8.54 (d), 7.44 (s), 7.33 (d), 7.27 (d), 7.26–7.08 (m), 7.05 (d), 7.01 (d), 6.98 (d), 6.88–6.78 (m), 6.43 (d), 5.93 (t), 5.77 (t), 5.32 (t), 5.08 (d), 5.02 (q), 4.90 (s), 4.83 (q), 4.67 (d), 4.57 (q), 3.96–3.82 (m), 3.34–3.20 (m), 2.80 (dt), 2.77–2.57 (m), 1.88–1.82 (m), 1.79–1.64 (m).

Example 18

2-(2-Oxo-2-(3,4,5-trimethoxyphenyl)-acetyl)-1,2,3,4-tetrahydroisoquinoline-3(S)-carboxylic acid 2-((7-pyridin-4-ylmethoxy)-1,2,3,4-tetrahydronaphthalen-1(S)-yl) ester (Compound 18)

Compound 18 was prepared according to Examples 5–7, but replacing (S)-Alloc-pipecolic acid with (S)-Alloc-3-carboxyl-1,2,3,4-tetrahydroisoquinoline and utilizing Compound 2(S). $^1$H NMR as a mixture of rotomers (500 MHz, CDCl13) δ8.61 (m), 7.41 (s), 7.40 (s), 7.31–6.96 (m), 6.88–6.80 (m), 6.47 (m), 5.88 (m), 5.74 (m), 5.39 (m), 5.07 (d), 4.87–4.74 (m), 4.60 (q), 3.98–3.82 (m), 3.28–3.18 (m), 2.02–1.62 (m), 1.53–1.45 (m).

Example 19

3-Benzyl-2(S)-((2-oxo-2-(3,4,5-trimethoxyphenyl-)acetyl) amino) propanoic acid ((7-pyridin-4-ylmethoxy)-1,2,3,4-tetrahydronaphthalen-1(R)-yl) ester (Compound 19)

Compound 19 was prepared according to Examples 5–7, but replacing (S)-Alloc-pipecolic acid with (S)-Alloc-phenylalanine and utilizing Compound 2(R). $^1$H NMR as a mixture of rotomers (500 MHz, CDCl$_3$) δ8.57 (dd), 7.66(s), 7.52 (d), 7.32–7.23 (m), 7.19 (d), 7.05 (d), 6.87 (m), 6.86 (s), 6.00 (t), 5.03 (q), 4.88 (q), 3.94 (s), 3.88 (s), 3.20 (dq), 2.78 (dt), 2.69–2.63 (m), 1.97–1.73 (m).

Example 20

3-Benzyl-2(S)-(methyl-(2-oxo-2-(3,4,5-trimethoxyphenyl)-acetyl) amino) propanoic acid ((7-pyridin-4-ylmethoxy)-1,2,3,4-tetrahydronaphthalen-1(R)-yl) ester (Compound 20)

Compound 20 was prepared according to Examples 5–7, but replacing (S)-Alloc-pipecolic acid with (S)-Alloc-N-methyl-phenylalanine and utilizing Compound 2(R). $^1$H NMR as a mixture of rotomers (500 MHz, CDCl$_3$) δ8.55 (d), 8.52 (d), 7.34 (s), 7.31–7.19 (m), 7.12 (m), 7.06–6.99 (m), 6.94–6.82 (m), 6.06 (t), 5.94 (t), 5.05 (q), 4.99 (q), 4.56 (q), 3.90 (s), 3.91 (s), 3.82 (s), 3.75 (s), 3.37 (dd), 3.28 (dd), 3.16 (dd), 3.08 (s), 2.99 (dd), 2.82–2.62 (m), 2.76 (s), 2.05–1.74 (m).

Example 21

3-Benzyl-2(S)-(methyl-(2-oxo-2-(3,4,5-trimethoxyphenyl)-acetyl)amino)propanoic acid ((7-pyridin-4-ylmethoxy)-1,2,3,4-tetrahydronaphthalen-1(S)-yl) ester (Compound 21)

Compound 21 was prepared according to Examples 5–7, but replacing (S)-Alloc-pipecolic acid with (S)-Alloc-N-methyl-phenylalanine and utilizing Compound 2(S). $^1$H NMR as a mixture of rotomers (500 MHz, CDCl$_3$) δ8.58 (dd), 8.53 (dd), 7.36 (d), 7.31–7.20 (m), 7.14 (s), 7.13–7.08 (m), 7.04 (d), 6.97 (dd), 6.88–6.84 (m), 6.04 (m), 5.18 (t), 5.13 (q), 4.98 (q), 4.53 (q), 3.89 (s), 3.88 (s), 3.78 (s), 3.67 (s), 3.44 (dd), 3.22 (dd), 3.19 (dd), 3.03 (s), 2.98 (dd), 2.82–2.62 (m), 2.78 (s), 2.01–1.87 (m), 1.83–1.73 (m).

Example 22

4-(6-Methyl-5,7-dimethoxyphenyl) butyric acid (Compound 22)

To a solution of 2,4-dimethoxybenzaldehyde (5.1 g, 28.3 mmol) and propanoic triphenylphosphonium bromide (14.4 g, 34.9 mmol) in methylene chloride (40 mL) at 0° C. was added 1.0M potassium t-butoxide in tetrahydrofuran (70 mmol). The reaction was allowed to warm to room temperature and stirred for 2 hr. The reaction was quenched by the addition of 2N hydrochloric acid and extracted with ethyl acetate (2×). The extracts were combined, washed with brine, dried over anhydrous magnesium sulfate, filtered and concentrated in vacuo. The residue was chromatographed on silica gel (elution with 5% methanol:methylene chloride) to provide 5.81 grams of a yellow oil. This material was dissolved in ethyl acetate (20 mL), treated with 10% palladium on carbon (581 mg) and hydrogenated at 40 psi. After 12 hr, the hydrogen was replaced with nitrogen, the reaction was filtered and concentrated in vacuo to provide 5.73 g of Compound 22.

Example 23

6-Methyl-5,7-dimethoxy-1,2,3,4-tetrahydronaphthalen-1-one (Compound 23)

To a solution of Compound 22 (5.73 g, 24.07 mmol) and 85% phosphoric acid (2.36 g, 24.07 mmol) in acetonitirle (50 mL) at 50° C. was added trifluoroacetic anhydride (3.5 mL, 25 mmol). After 15 min, the reaction was cooled, diluted with ethyl acetate and washed with water, 10% sodium bicarbonate, brine, dried over anhydrous magnesium sulfate, filtered and concentrated in vacuo. Chromatography of the residue on silica gel (elution with 5% ethyl acetate:hexanes) provided 3.54 g of Compound 23.

Example 24

6-Methyl-5,7-dipropoxy-1,2,3,4-tetrahydronaphthalen-1-one (Compound 24)

To a solution of Compound 23 (3.54 g, 16.1 mmol) in toulene (50 mL was added aluminum chloride (10.7 g, 80.5 mmol) in portions. Once the addition was complete, the mixture was heated to reflux, stirred for 30 min and cooled to 0° C. The reaction was quenched by the addition of 1N hydrochloric acid and the product extract with ethyl acetate (2×). The extracts were combined, washed with water, brine, dried over anhydrous magnesium sulfate, filtered and concentrated in vacuo. The residue was passed through a plug of silica gel (elution with 20% ethyl acetate:hexanes) to provide 2.78 g of diol. This material was dissolved in 2-butanone (25 mL), treated with 1-bromopropane (6.6 mL, 72.6 mmol) and powdered potassium carbonate (9.68 g, 72.6 mmol) and heated to reflux. After 12 hr the reaction was cooled, diluted with water and extracted with ethyl acetate (2×). The extracts were combined, washed with water, brine, dried over anhydrous magnesium sulfate, filtered and concentrated in vacuo. Chromatography of the residue on silica gel (elution with 10% ethyl acetate:hexanes) provided 3.42 g of Compound 24.

Example 25

6-methyl-5,7-dipropoxy-2-pyridin-3-ylmethlene-3,4-dihydro-2H-naphthalen-1-one (Compound 25)

To a solution of Compound 24 (3.42 g, 12.4 mmol) and 3-pyridinecarboxadehyde (1.59 g, 14.9 mmol) in abs. ethanol (25 mL) was added potassium hydroxide (350 mg, 6.2 mmol and the reaction allowed to stir for 15 min. The reaction was concentrated and the residue dissolved in ethyl acetate washed with water, brine, dried over anhydrous magnesium sulfate, filtered and concentrated in vacuo. Chromatography of the residue on silica gel (elution with 50% ethyl acetate:hexanes) provided 4.26 g of Compound 25 as an off white solid.

Example 26

6-Methyl-5,7-dipropoxy-2-(pyridin-3-ylmethyl)-1,2,3,4-tetrahydronaphthalen-1-one (Compound 26)

A mixture of Compound 25 (3.96 g, 10.8 mmol) and 10% palladium on carbon (600 mg) in abs. methanol (100 mL) was hydrogenated at 1 atm for 12 hr. The hydrogen was replaced with nitrogen, the reaction was filtered and concentrated in vacuo. Chromatography of the residue on silica gel (elution with 20% ethyl acetate:hexanes) provided 2.72 g of Compound 26.

Example 27

Syn-6-Methyl-5,7-dipropoxy-2-(pyridin-3-ylmethyl)-1,2,3,4-tetrahydronaphthalen-1-ol Compound (27) and Anti-6-Methyl-5,7-dipropoxy-2-(pyridin-3-ylmethyl)- 1,2,3,4-tetrahydronaphthalen-1-ol (Compound 28)

To a solution of Compound 26 (1.10 g, 2.98 mmol) in abs. methanol (10 mL) was slowly added sodium borohydride (226 mg, 2.98 mmol). After stirring for 1 hr, the reaction was concentrated and the residue partitioned between ethyl acetate and water. The layers were separated and the organic phase was washed with brine, dried over anhydrous magnesium sulfate, filtered and concentrated in vacuo. Chromatography of the residue on silica gel (elution with 10% ethyl acetate:hexanes) provided 502 mg of Compound 27. Further elution provided 475 mg of Compound 28.

Example 28

1-2-Oxo-2-(3,4,5-trimethoxyphenyl)acetyl)piperidine-2(S)-carboxylic acid (6-methyl-5,7-dipropoxy-2(R)-(pyridin-3-ylmethyl)-1,2,3,4-tetrahydronaphthalen-1(S)-yl) ester and 1-(2-Oxo-2-(3,4,5-trimethoxyphenyl)-acetyl) piperidine-2(S)-carboxylic acid (6-methyl-5,7-dipropoxy-2(S)-(pyridin-3-ylmethyl)-1,2,3,4-tetrahydronaphthalen-1(R)-yl) ester (Compound 29A and 29B)

Compounds 29A and 29B were prepared as described in Examples 5–7, but replacing Compound 2 with Compound 27 to provide a diastereomeric mixture. Chromatography of the mixture on silica gel (elution 10% acetone:hexanes) provided Compound 29A. Further elution provided Compound 29B.

Compound 29A: $^1$H NMR as a mixture of rotomers (500 MHZ, $CDCl_3$) δ8.54–8.43 (m), 7.60 (d), 7.41 (s), 7.31 (s), 7.30–7.28 (m), 6.61 (s), 6.57 (s), 5.97 (d), 5.93 (d), 5.40 (d), 4.63 (br d), 4.43 (d), 3.98 (s), 3.97–3.68 (m), 3.93 (s), 3.89 (s), 3.50 (br d), 3.32 (dt), 3.22 (dt), 3.01 (dt), 2.91 (m), 2.78 (dq), 2.56 (quintet), 2.44 (m), 2.23–2.10 (m), 2.17 (s), 1.85–1.71 (m), 1.69–1.49 (m), 1.1 (t), 1.03 (t), 1.00 (t).
Compound 29B: $^1$H NMR as a mixture of rotomers (500 MHZ, $CDCl_3$) δ8.49 (s), 8.47 (s), 7.54 (m), 7.36 (s), 7.38–7.21 (m), 6.62 (s), 6.53 (s), 6.03 (d), 5.39 (d), 4.55 (br d), 4.38 (d), 3.96 (s), 3.95 (s), 3.93 (s), 3.90 (s), 3.83 (dt), 3.69 (dt), 3.48 (q), 3.44 (br d), 3.16 (dt), 3.00 9br d), 2.83 (dd), 2.72–2.49 (m), 2.45 (br d), 2.18 (m), 2.15 (s), 2.14 (s), 1.94–1.68 (m), 1.61(m), 1.49 (m), 1.35 (m), 1.20 (t), 1.04 (t), 0.97 (t).

Example 29

1-(2-Oxo-2-(3,4,5-trimethoxyphenyl)acetyl)piperidine-2(S)-carboxylic acid (6-methyl-5,7-dipropoxy-2(R)-(pyridin-3-ylmethyl)-1,2,3,4-tetrahydronaphthalen-1 (R)-yl) ester and 1-(2-Oxo-2-(3,4,5-trimethoxyphenyl)-acetyl) piperidine-2(S)-carboxylic acid (6-methyl-5,7-dipropoxy-2 (S)-(pyridin-3-ylmethyl)-1,2,3,4-tetrahydronaphthalen-1(S)-yl) ester (Compound 30A and 30B)

Compounds 30A and 30B were prepared as described in Examples 5–7, but replacing Compound 2 with Compound 28 to provide a diastereomeric mixture. Chromatography of the mixture on silica gel (elution 10% acetone:hexanes) provided Compound 30A. Further elution provided Compound 30B.

Compound 30A: $^1$H NMR as a mixture of rotomers (500 MHZ, $CDCl_3$) δ8.48 (m), 7.57 (m), 7.37 (s), 7.33–7.27 (m), 7.20 (s), 6.51 (s), 6.49 (s), 5.85 (d), 5.38 (d), 4.60 (br d), 4.39 (d), 3.97 (s), 3.95–3.28 (m), 3.94 (s), 3.87 (s), 3.73 (t), 3.50 (dd), 3.30 (dt), 2.98 (dt), 2.84–2.65 (m), 2.51 (dd), 2.42 (br d), 2.32 (m), 2.17 (t), 1.98 (m), 1.87–1.73 (m), 1.68–1.50 (m), 1.47 (m), 1.09 (t), 1.07 (t), 1.04 (t), 0.99 (t).
Compound 30B: $^1$H NMR as a mixture of rotomers (500 MHZ, $CDCl_3$) δ8.49 (m), 8.43 (d), 8.32(d), 7.57 (m), 7.36 (s), 7.35 (s), 7.30–7.25 (m), 7.18 (s), 6.63 (s), 6.48 (s), 6.35 (s), 6.02 (d), 5.87 (d), 5.77 (d), 5.38 (m), 4.66 (br d), 4.44 (d), 3.98–3.67 (m), 3.52 (br d), 3.44 (br d), 3.33 (dt), 3.26 (dt), 3.14 (dt), 3.01 (br d), 2.88–2.49 (m), 2.32 (m), 2.17 (s), 2.16 (s), 2.12 (s), 2.01 (m), 1.87–1.72 (m), 1.68–1.53 (m), 1.09 (t), 1.04(t), 1.02 (t), 0.98 (t).

Example 30

MDR Sensitization assays

To assay the ability of the compounds according to this invention to increase the antiproliferative activity of a drug, cell lines which are known to be resistant to a particular drug may be used. These cell lines include, but are not limited to, the L1210, P388D, CHO and MCF7 cell lines. Alternatively, resistant cell lines may be developed. The cell line is exposed to the drug to which it is resistant, or to the test compound; cell viability is then measured and compared to the viability of cells which are exposed to the drug in the presence of the test compound.

We have carried out assays using L1210 mouse leukemia cells transformed with the pHaMDR1/A retrovirus carrying a MDR1 cDNA, as described by Pastan et al., *Proc. Natl.*

*Acad. Sci. USA*, 85, pp. 4486–4490 (1988). The resistant line, labeled L1210VMDRC.06, was obtained from Dr. M. M. Gottesman of the National Cancer Institute. These drug-resistant transfectants had been selected by culturing cells in 0.06 mg/ml colchicine.

Multi-drug resistance assays were conducted by plating cells ($2 \times 10^3$, $1 \times 10^4$, or $5 \times 10^4$ cells/well) in 96 well microtiter plates and exposing them to a concentration range of doxorubicin (50 nM-10 µM) in the presence or absence of multi-drug resistance modifier compounds ("MDR inhibitors") of this invention (0.5, 1.0 or 2.5 µM) as described in Ford et al., *Cancer Res.*, 50, pp. 1748–1756 (1990). After culture for 3 days, the viability of cells was quantitated using MTT (Mossman) or XTT dyes to assess mitochondrial function. All determinations were made in replicates of 4 or 8. Also see, Mossman T., *J. Immunol. Methods*, 65, pp. 55–63 (1983).

Results were determined by comparison of the IC50 for doxorubicin alone to the IC50 for doxorubicin+MDR inhibitor. An MDR ratio was calculated (IC50 Dox/IC50 Dox+Inhibitor) and the integer value used for comparison of compound potencies.

In all assays, compounds according to this invention were tested for intrinsic antiproliferative or cytotoxic activity. The results are summarized in Table 2 below.

TABLE 2

Evaluation of Compounds for Reversal of MDR in L1210vDOX

| Cpd | $IC_{50}$ DOX Alone | $IC_{50}$ DOX + 0.5 µM Cpd | $IC_{50}$ DOX + 1.0 µM Cpd | $IC_{50}$ DOX + 2.5 µM Cpd | $IC_{50}$ DOX + 0.5 µM Cpd | $IC_{50}$ DOX + 1.0 µM Cpd | $IC_{50}$ DOX + 2.5 µM Cpd |
|---|---|---|---|---|---|---|---|
| 6 | 475 | 100 | 75 | 50 | 4.8 | 6.3 | 9.5 |
| 7 | 475 | 225 | 100 | 50 | 23.1 | 4.8 | 9.5 |
| 9 | 4800 | 750 | 350 | 175 | 6.4 | 13.7 | 22.8 |
| 11A | 700 | 650 | 350 | 175 | 1.1 | 2.0 | 4.0 |
| 11B | 700 | 400 | 325 | 70 | 1.8 | 2.2 | 10.0 |
| 15 | 425 | 70 | <50 | <50 | 6.1 | >8.5 | >8.5 |
| 16 | 425 | 190 | 60 | <50 | 2.2 | 7.1 | >8.5 |
| 17 | 2000 | 360 | 230 | 180 | 5.6 | 8.7 | 11.1 |
| 18 | 2000 | 600 | 300 | 200 | 3.3 | 6.7 | 10.0 |
| 19 | 475 | 300 | 200 | 75 | 1.6 | 2.4 | 6.3 |
| 20 | 525 | 175 | 75 | <50 | 3.0 | 7.0 | 10.5 |
| 21 | 650 | 120 | 95 | 75 | 5.4 | 6.8 | 8.7 |
| 29A | 350 | 250 | 190 | <50 | 1.4 | 1.8 | >7.0 |
| 29B | 350 | 200 | 95 | <50 | 1.8 | 3.7 | >7.0 |
| 30A | 350 | 250 | 150 | <50 | 1.4 | 2.3 | >7.0 |
| 30B | 350 | 250 | 175 | <50 | 1.4 | 2.0 | >7.0 |

EXAMPLE 32

Inhibition of MRP-Mediated MDR

In order to demonstrate that the compounds of this invention are effective in reversing MPR-mediated MDR, in addition to P-glycoprotein-mediated MDR, we assayed inhibition in a non-P-glycoprotein expressing cell line.

We plated HL60/ADR cells in 96 well microtiter plates ($4 \times 10^4$ cells/well). The cells were then exposed to various concentrations of doxorubicin (50 nM to 10 µM) in the presence or absence of various compounds of this invention at various concentrations (0.5–10 µM). After culturing the cells for 3 days, their viability was quantitated using the XTT dye method to assess mitochondrial function. Results were expressed as a ratio of the $IC_{50}$ for doxorubicin alone to the $IC_{50}$ for doxorubicin plus MDR inhibitor. $IC_{50}$ values are expressed in nM. In all assays the intrinsic antiproliferative or cytotoxicity activity of the MDR inhibitors was also determined for HL60/ADR cells. The results of this assay are set forth in Table 3 below:

TABLE 3

| | Reversal Of MRP-mediated MDR in HL60/ADR Cells | | | | | | |
|---|---|---|---|---|---|---|---|
| Cpd | $IC_{50}$ DOX Alone | $IC_{50}$ DOX + 0.5 µM Cpd | $IC_{50}$ DOX + 1.0 µM Cpd | $IC_{50}$ DOX + 2.5 µM Cpd | $IC_{50}$ DOX + 0.5 µM Cpd | $IC_{50}$ DOX + 1.0 µM Cpd | $IC_{50}$ DOX + 2.5 µM Cpd |
| 6 | 3500 | 400 | 550 | 90 | 8.8 | 6.4 | 39 |
| 16 | 3500 | 1500 | 90 | <50 | 2.3 | 39 | >60 |
| 17 | 3500 | 1500 | 300 | 300 | 2.3 | 11.7 | 11.7 |
| 21 | 3500 | 1000 | 1100 | 150 | 3.5 | 3.2 | 23 |

While we have described a number of embodiments of this invention, it is apparent that our basic constructions may be altered to provide other embodiments which utilize the products, processes and methods of this invention. Therefore, it will be appreciated that the scope of this invention is to be defined by the appended claims, rather than by the specific embodiments which have been presented by way of example.

I claim:

1. A compound represented by formula (I):

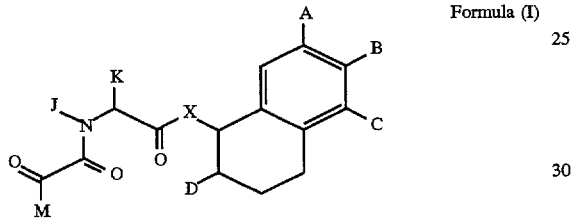

Formula (I)

and pharmaceutically acceptable salts thereof, wherein:

A, B and C are independently selected from hydrogen, halogen, (C1–C6)-straight or branched alkyl, O—(C1–C6)-straight or branched alkyl, $(CH_2)_n$—Ar or $Y(CH_2)_n$—Ar; wherein Y is O, S or $NR_1$; wherein $R_1$ is (C1–C6)-straight or branched alkyl and hydrogen;

n is an integer from 0 to 4; and

Ar is a carbocyclic aromatic group selected from the group consisting of phenyl, 1-naphthyl, 2-naphthyl, indenyl, azulenyl, fluorenyl and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, peridinyl, carbazolyl, acridinyl, phenazinyl, phenothiazinyl and phenoxazinyl; and wherein:

Ar may contain one or more substituents independently selected from the group consisting of: hydrogen, hydroxyl, halogen, nitro, $SO_3H$, trifluoromethyl, trifluoromethoxy, (C1–C6)-straight or branched alkyl, O—(C1–C6)-straight or branched alkyl, O-benzyl, O-phenyl, 1,2-methylenedioxy, carboxyl, morpholinyl, piperidinyl and $NR_2R_3$ and $NR_2R_3$ carboxamides; wherein $R_2$ and $R_3$ are independently selected from hydrogen, (C1–C5)-straight or branched alkyl and benzyl;

D is selected from the group consisting of hydrogen or $(CH_2)_m$—E; wherein

E is Ar or $NR_4R_5$; wherein $R_4$ and $R_5$ are independently selected from hydrogen, (C1–C5)-straight or branched alkyl and $(CH_2)$Ar or can be taken together to form a 5 or 6 membered heterocyclic ring; and m is an integer from 1 to 3;

X is O or $NR_6$; wherein $R_6$ is selected from the group consisting of hydrogen, (C1–C6)-straight or branched alkyl and $(CH_2)_m$—Ar;

J and K are independently (C1–C6)-straight or branched alkyl or Ar-substituted with (C1–C6)-straight or branched alkyl or wherein J and K are taken together to form a five or six membered ring or a five or six membered benzo-fused ring;

M is (C1–C6)-straight or branched alkyl or Ar; and the stereochemistry at carbon 1 and carbon 2 is independently selected from R or S.

2. The compound according to claim 1 represented by formula (II):

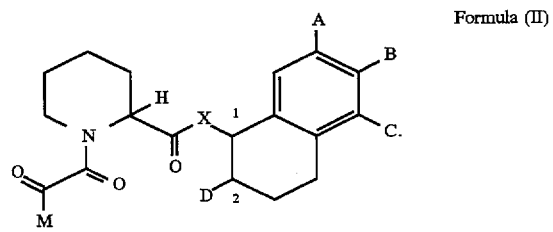

Formula (II)

3. The compound according to claim 1 represented by formula (III):

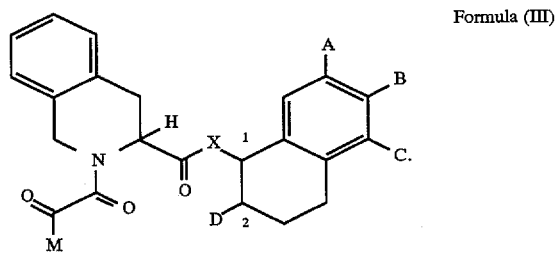

Formula (III)

4. The compound according to claim 1 represented by formula (IV):

Formula (IV)

[chemical structure diagram with labels A, B, C, D, J, K, M, N, O, X]

wherein J is selected from methyl or hydrogen and K is selected from (C1–C6)-straight or branched alkyl or (CH$_2$)$_m$—Ar.

5. The compound according to claim 4, wherein K is benzyl.

6. The compound according to any one of claims 1 to 5, wherein:

A and C are independently selected from O—CH$_2$-4-pyridine, O-propyl or hydrogen;

B is selected from O—CH$_2$-4-pyridine, O-propyl or hydrogen; and

D is selected from CH$_2$-3-pyridine or hydrogen.

7. The compound according to any one of claims 1 to 5, wherein M is 3,4,5-trimethoxyphenyl.

8. The compound according to any one of claims 1 to 5, wherein X is selected from oxygen, NH$_2$ and N-benzyl.

9. The compound according to claim 2, selected from:

1-(2-oxo-2-(3,4,5-trimethoxyphenyl)-acetyl)-piperidine-2(S)-carboxylic acid 2-((7-pyridin-4-ylmethoxy)-1,2,3,4-tetrahydronaphthalen-1(S)-yl)ester (compound 6);

1-(2-oxo-2-(3,4,5-trimethoxyphenyl)-acetyl)-piperidine-2(S)-carboxylic acid 2-((7-pyridin-4-ylmethoxy)-1,2,3,4-tetrahydronaphthalen-1(R)-yl)ester (compound 7);

1-(2-oxo-2-(3,4,5-trimethoxyphenyl)-acetyl)-piperidine-2(S)-carboxylic acid 2-((6-pyridin-4-ylmethoxy)-1,2,3,4-tetrahydronaphthalen-1-yl)ester (compound 8);

1-(2-oxo-2-(3,4,5-trimethoxyphenyl)-acetyl)-piperidine-2(S)-carboxylic acid 2-((5-pyridin-4-ylmethoxy)-1,2,3,4-tetrahydronaphthalen-1-yl)ester (compound 9);

1-(2-oxo-2-(3,4,5-trimethoxyphenyl)-acetyl)-piperidine-2(S)-carboxylic acid 2-((7-pyridin-4-ylmethoxy)-1,2,3,4-tetrahydronaphthalen-1(R)-yl)amide (compound 11A);

1-(2-oxo-2-(3,4,5-trimethoxyphenyl)-acetyl)-piperidine-2(S)-carboxylic acid 2-((7-pyridin-4-ylmethoxy)-1,2,3,4-tetrahydronaphthalen-1(S)-yl)amide (compound 11B);

1-(2-oxo-2-(3,4,5-trimethoxyphenyl)-acetyl)-piperidine-2(S)-carboxylic acid 2-(N-benzyl(7-pyridin-4-ylmethoxy)-1,2,3,4-tetrahydronaphthalen-1(R)-yl)amide (compound 15);

1-(2-oxo-2-(3,4,5-trimethoxyphenyl)-acetyl)-piperidine-2(S)-carboxylic acid 2-(N-benzyl(7-pyridin-4-ylmethoxy)-1,2,3,4tetrahydronaphthalen-1-yl)amide (compound 16);

1-(2-oxo-2-(3,4,5-trimethoxyphenyl)-acetyl)-piperidine-2(S)-carboxylic acid (6-methyl-5,7-dipropoxy-2(R)-(pyridin-3-ylmethyl)-1,2,3,4-tetrahydronaphthalen-1(S)-yl)ester (compound 29A);

1-(2-oxo-2-(3,4,5-trimethoxyphenyl)-acetyl)-piperidine-2(S)-carboxylic acid (6-methyl-5,7-dipropoxy-2(S)-(pyridin-3-ylmethyl)-1,2,3,4-tetrahydronaphthalen-1(R)-yl)ester (compound 29B);

1-(2-oxo-2-(3,4,5-trimethoxyphenyl)-acetyl)-piperidine-2(S)-carboxylic acid (6-methyl-5,7-dipropoxy-2(R)-(pyridin-3-ylmethyl)-1,2,3,4-tetrahydronaphthalen-1(R)-yl)ester (compound 30A); or 1-(2-oxo-2-(3,4,5-trimethoxyphenyl)-acetyl)-piperidine-2(S)-carboxylic acid (6-methyl-5,7-dipropoxy-2(S)-(pyridin-3-ylmethyl)-1,2,3,4- tetrahydronaphthalen-1(S)-yl)ester (compound 30B).

10. The compound according to claim 3, selected from:

2-(2-oxo-2-(3,4,5-trimethoxyphenyl)-acetyl)-1,2,3,4-tetrahydroisoquinoline-3(S)-carboxylic acid 2-((7-pyridin-4-ylmethoxy)-1,2,3,4-tetrahydronaphthalen-1(R)-yl)ester (compound 17); or 2-(2-oxo-2-(3,4,5-trimethoxyphenyl)-acetyl)-1,2,3,4-tetrahydroisoquinoline-3(S)-carboxylic acid 2-((7-pyridine-4-ylmethoxy)-1,2,3,4-tetrahydronaphthalen-1(S)-yl)ester (compound 18).

11. The compound according to claim 5, selected from:

3-benzyl-2(S)-((2-oxo-2-(3,4,5-trimethoxyphenyl)-acetyl) amino)propanoic acid ((7-pyridin-4-ylmethoxy)-1,2,3,4-tetrahydronaphthalen-1(R)-yl)ester (compound 19);

3-benzyl-2(S)-(methyl-(2-oxo-2-(3,4,5-trimethoxyphenyl)-acetyl)amino)propanoic acid ((7-pyridin-4-ylmethoxy)-1,2,3,4-tetrahydronaphthalen-1(R)-yl)ester (compound 20); or 3-benzyl-2(S)-(methyl-(2-oxo-2-(3,4,5-trimethoxyphenyl)-acetyl)amino)propanoic acid ((7-pyridine-4-ylmethoxy)-1,2,3,4-tetrahydronaphthalen-1(S)-yl)ester (compound 21).

12. A pharmaceutical composition for treatment and prevention of multi-drug resistance comprising:

a. an amount of a compound according to any one of claims 1 to 5 or 9 to 11 effective to reduce multi-drug resistance; and b. A physiologically acceptable adjuvant, carrier or vehicle.

13. The pharmaceutical composition according to claim 12, further comprising a chemotherapeutic agent.

14. The pharmaceutical composition according to claim 12 further comprising a chemosensitizer.

15. A method for treating of preventing multi-drug resistance, comprising the step of administering to said patient a composition according to claim 12.

16. The method according to claim 15, wherein said composition is administered orally.

17. The method according to claim 16, wherein said multi-drug resistance is P-glycoprotein-mediated.

18. The method according to claim 17, wherein said multi-drug resistance is MRP-mediated.

19. A method for treating or preventing multi-drug resistance, comprising the step of administering to said patient a composition according to claim 13.

20. A method for treating or preventing multi-drug resistance, comprising the step of administering to said patient a composition according to claim 14.

* * * * *

UNITED STATES PATENT AND TRADEMARK OFFICE
CERTIFICATE OF CORRECTION

PATENT NO : 5,726,184

DATED : March 10, 1998

INVENTION(S) : Robert Edward Zelle

It is certified that error appears in the above-identified patent and that said Letters Patent is hereby corrected as shown below:

Column 2, line 29 delete "resistant" and substitute therefor -- resistance --.
Column 4, line 43 delete "formula" and substitute therefor -- formulae --.
Column 9, line 22 and column 26, line 47 delete "of" and substitute therefor -- or --.
Column 9, line 25 delete "humans. And" and substitute therefor -- humans, and --.
Column 14, line 13 delete "trimethoxybenzyolformic" and substitute therefor -- trimethoxybenzoylformic --.
Column 16, line 41 delete "m g" and substitute therefor -- mg --.
Column 16, line 51 delete "neutalized" and substitute therefor -- neutralized --.
Column 18, line 25 delete "dimethoxybenzaldehdye" and substitute therefor -- dimethoxybenzaldehyde --.
Column 20, line 16 delete "9br d)," and substitute therefor -- (br d), --.
Column 21, Table 2, Compound 7 delete "23.1" and substitute therefor -- 2.1 --.

UNITED STATES PATENT AND TRADEMARK OFFICE
CERTIFICATE OF CORRECTION

PATENT NO. : 5,726,184
DATED : March 10, 1998
INVENTOR(S) : Robert Edward Zelle

It is certified that error appears in the above-identified patent and that said Letters Patent is hereby corrected as shown below:

Column 23, Table 3 delete
"

| Cpd | $IC_{50}$ DOX alone | $IC_{50}$ DOX + 0.5µM Cpd | $IC_{50}$ DOX + 1.0µM Cpd | $IC_{50}$ DOX + 2.5µM Cpd | $IC_{50}$ DOX + 0.5µM Cpd | $IC_{50}$ DOX + 1.0µM Cpd | $IC_{50}$ DOX + 2.5µM Cpd |
|---|---|---|---|---|---|---|---|

"

and substitute therefor
--

| Cpd | $IC_{50}$ DOX alone | $IC_{50}$ DOX + 2.5µM Cpd | $IC_{50}$ DOX + 5.0µM Cpd | $IC_{50}$ DOX + 10.0µM Cpd | $IC_{50}$ DOX + 2.5µM Cpd | $IC_{50}$ DOX + 5.0µM Cpd | $IC_{50}$ DOX + 10.0µM Cpd |
|---|---|---|---|---|---|---|---|

--.

Signed and Sealed this

Twelfth Day of December, 2000

Q. TODD DICKINSON

Attest:

*Attesting Officer*     *Director of Patents and Trademarks*